United States Patent [19]

Lekholm

[11] Patent Number: 5,042,463

[45] Date of Patent: Aug. 27, 1991

[54] PATCH ELECTRODE FOR HEART DEFIBRILLATOR

[75] Inventor: Anders Lekholm, Northridge, Calif.

[73] Assignee: Siemens-Pacesetter, Inc., Sylmar, Calif.

[21] Appl. No.: 527,622

[22] Filed: May 23, 1990

[51] Int. Cl.⁵ ............................................. A61N 1/05
[52] U.S. Cl. .................................. 128/784; 128/642
[58] Field of Search ............... 128/639, 640, 642, 784, 128/785, 419 P

[56] References Cited

U.S. PATENT DOCUMENTS

| D. 273,514 | 4/1984 | Heilman et al. | 128/419 D |
|---|---|---|---|
| 4,030,509 | 6/1977 | Heilman et al. | 128/419 D |
| 4,291,707 | 9/1981 | Heilman et al. | 128/784 |
| 4,628,937 | 12/1986 | Hess et al. | 128/642 |
| 4,827,932 | 5/1989 | Ideker et al. | 128/419 D |

Primary Examiner—William E. Kamm
Assistant Examiner—Scott M. Getzow
Attorney, Agent, or Firm—Malcolm J. Romano

[57] ABSTRACT

A flexible, planar patch electrode for cardiac defibrillation is fabricated from conductive wire mesh covered on an insulation side by a flexible layer of insulation. The electrode provides a substantial electrical contact area of 2-4 square inches and is shaped to provide an essentially rectangular base region with a plurality of protrusions extending longitudinally therefrom. he protrusions may be readily flexed to follow natural heart contours and slots between protrusions may be positioned to avoid features such as arteries near the surface of the heart. Central attachment of a lead within the base region minimizes current density and corresponding I²R energy losses.

19 Claims, 2 Drawing Sheets

PATCH ELECTRODE FOR HEART DEFIBRILLATOR

BACKGROUND OF THE INVENTION

Heart fibrillation is a high frequency arrhythmia of one or more chambers of the heart. It results in a loss of proper heart pumping action and a corresponding loss of blood circulation.

It is known that fibrillation can be arrested by passing an electric current of sufficient strength through the fibrillating heart. The electric field causes a depolarization of the heart muscle or myocardium. If this depolarization extends to a sufficient amount of the heart tissue, defibrillation can be achieved.

If the fibrillation occurs in a clinical environment, such as a hospital where defibrillation equipment is usually readily available, a pair of disc shaped paddles can be placed upon the chest of the patient. When sufficient electrical energy is applied to the paddles, the required electrical field can be established in the heart. However, this presupposes that fibrillation is detected in time and that the necessary equipment is close at hand.

An alternative solution is to attach a set of electrodes directly to the heart. This would typically be done when access to the heart is provided by open heart surgery or some other surgical procedure. Because the electrodes are attached directly to the heart, the electrical energy required to accomplish defibrillation is much less than the energy required for paddles placed externally on the chest at a substantial distance from the heart.

For people prone to fibrillation symptoms, then it thus becomes practical to implant in the body of a patient a defibrillator that continuously monitors heart activity and automatically and immediately establishes a depolarizing electrical field upon detection of fibrillation.

When the depolarizing electrical field is supplied by an implanted battery, the field must be generated with the expenditure of a minimum amount of electrical energy in order to optimize battery life. Even small energy losses can be important when the energy must be supplied by an implanted battery. It thus becomes difficult to satisfy conflicting demands of physiological factors and electrical energy consumption factors.

From the physiological point of view it is desirable to minimize interference with the operation of the heart. A point contact connected by an extremely flexible wire would be an ideal electrode from the physiological perspective. However, such an arrangement would be less than optimum from the electrical point of view, since it would not provide a uniform electric field in the heart desirable for effective depolarization.

In order to accomplish defibrillation it is necessary to establish a minimum strength depolarizing electrical field throughout a substantial portion of the myocardium. As one would expect, the depolarizing electrical field strength from a small electrode is a maximum at the electrode and decreases as a function of distance from the electrode. From the electrical point of view it is thus desirable to have a large electrode contacting a substantial surface area of the myocardium.

Although the large surface area electrode is ideal from the electrical point of view, it is physiologically unsatisfactory because it imposes a physical restraint upon the heart. The heart must beat continuously about 60 beats per minute and even the slightest interference becomes significant after millions of repetitions. If a heart is of a condition to be in danger of fibrillation to start with, any interference with heart activity becomes even more significant. A compromise is thus generally made between the point contact that is physiologically desirable and the large surface area electrode that is electrically desirable.

U.S. Pat. No. 4,827,932 to Ideker et al. teaches a set of large surface area flat patch electrodes in FIGS. 6a, 6b and 6c which are intended to cover as much of the ventricular surface area of the heart as is possible without inducing large current flows directly between pairs of adjacent electrodes through vascular passages. In the arrangement of FIG. 6b the patch is partially bifurcated to form two projections that may be conformably wrapped about the heart. A laterally connected lead gives rise to a high current density in a base region as current flows past the bifurcation toward the projection farthest from the lead connection point. With such a configuration, the electrical losses which result from the non-uniform current densities can be substantial relative to the available energy from an implanted battery. In addition, the large patch size necessarily imposes a significant restriction upon the expansion and contraction of the heart muscle.

U.S. Pat. No. 4,030,509 to Heilman et al. teaches various arrangements of patch electrodes including a large, contoured electrode for placement at the base of the heart. U.S. Pat. No. 4,291,707 and Des. 273,514 to Heilman et al. teach various arrangements of relatively inflexible flat planar electrodes. Such arrangements do not readily provide substantial contact area without perceptibly impeding the pumping action of the heart.

SUMMARY OF THE INVENTION

A flexible, planar patch electrode for cardiac defibrillation in accordance with the invention is fabricated from a sheet of a conductive mesh with a layer of Dacron-reinforced Silastic sheeting secured to the noncontact side to provide insulation. The electrode has a generally rectangular base portion with two or more protrusions separated by slots extending longitudinally from the base portion.

A tantalum coil within silicone tubing preferably extends about the periphery of the mesh to make the electrode more readily visible on X-ray photographs. The insulation layer extends a short distance beyond the periphery of the titanium mesh to ensure good insulation of the mesh and to provide a peripheral surface through which sutures may be passed to secure the electrode to a heart. Silastic sheeting is sufficiently soft to permit passage of a suture needle therethrough, but may optionally have preformed suture apertures in the periphery thereof.

A lead is conductively secured to the base portion of the electrode as by welding or crimping with the point of attachment being centrally located between the sides of the base. The central placement minimizes current density past the slots separating the individual protrusions to correspondingly minimize resistive electrical losses in the patch.

BRIEF DESCRIPTION OF THE DRAWINGS

A better understanding of the invention may be had from a consideration of the following Detailed Description, taken in conjunction with the accompanying drawings in which.

DETAILED DESCRIPTION

Figure 1:
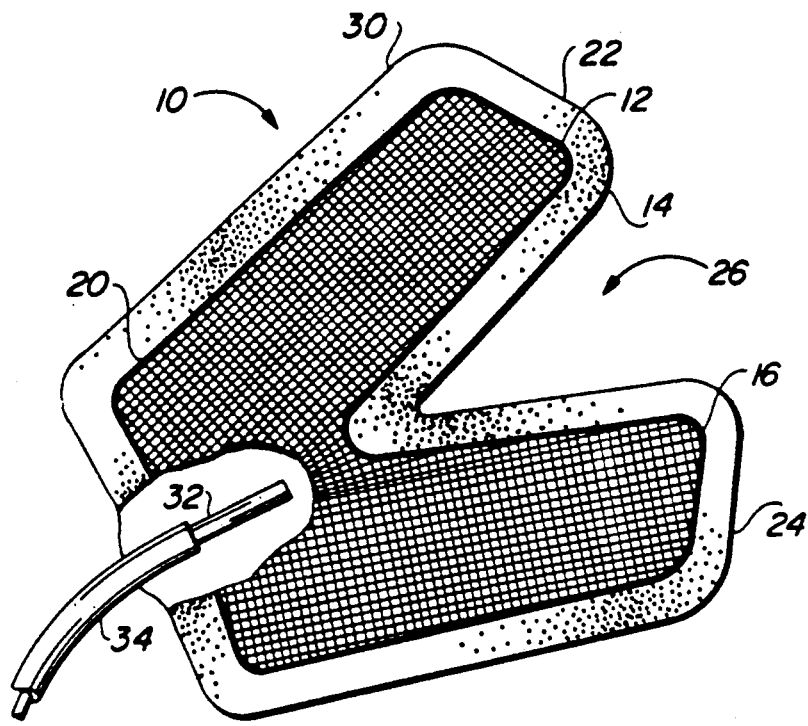
FIG. 1 is a plan view, partly broken away, taken from the contact side, of a titanium mesh patch electrode for cardiac defibrillation in accordance with the invention.

Referring now to FIG. 1, a planar, highly flexible patch electrode 10 for cardiac defibrillation in accordance with the invention includes a layer of foraminous mesh 12 having a layer of insulating material 14 such as Dacron reinforced Silastic sheeting bonded thereto. A radiopaque marker 16 is formed by interweaving about the periphery of the mesh 12 a tantalum coil that is disposed within an electrically insulating sealed silicone tube. The mesh 12 is a flexible planar screen formed preferably of titanium wire. Other materials appropriate for the screen are carbon, metal carbide, metal nitride, and metal oxide. Furthermore, the patch may be completely surface-coated by the carbon and the metal compounds noted. The metals of course should be nontoxic, biocompatible, which is well known in the art.

The electrode preferably has a conductive mesh surface area in the range of 2-4 square inches to provide substantial spatial distribution of an applied electric field without being so large as to lose flexibility or otherwise interfere with the normal beating of a heart to which it is attached. An area of substantially 3 square inches is preferred.

The electrode 10 is shaped to provide a generally rectangular base area 20 having two elongated protrusions 22, 24 extending longitudinally therefrom. The protrusions 22, 24 have a generally rectangular shape with rounded corners and are separated by an intermediate slot 26. The use of a plurality of protrusions 22, 24, together with the inherently flexible nature of the insulated titanium mesh patch enable the electrode 10 to be readily shaped to match the contours of a section of a heart to which it is attached. The protrusions may also have a gently curved shape to better match the anatomy of the heart. After being secured, the low mass patch electrode 10 can continue to flex as necessary to remain in conformity with the beating heart while offering minimal interference with the normal motion of the heart surface.

The slot 26 enables the electrode 10 to be adaptively located on the surface of the heart so as to straddle or otherwise avoid large blood vessels or other features that might cause a degradation of optimal heart activity, or pose a risk during defibrillation.

The periphery 30 of the thin insulating layer 14 is sufficiently soft and pliant that a needle may be used to pass sutures (not shown) therethrough to secure the electrode to the myocardium in a conventional manner. Alternatively, preformed holes or tabs (not shown) may be disposed about the periphery 30 of insulating layer 14 to make it even easier to suture the lead to the myocardium.

A conductive lead 32 is surrounded by an insulating tube 34 and conventionally secured as by welding or crimping to the noncontact side of the mesh 12 at a position that is centrally located laterally within the base region. The insulation tube 34 extends to beneath the insulating layer 14 so that the noncontact side of the electrode 10 remains fully electrically insulated to protect surrounding tissue. The conductive lead 32 extends beyond insulating tube 34 to enable conductive securement to the foraminous layer 12.

The central location of the weld within the base region helps to minimize current density and hence resistive losses in the patch. In the double protrusion version of FIG. 1 the current divides at the weld point to pass to the two separate protrusions. This contrasts with prior art contact arrangements wherein all of the current for one of the protrusions must pass a constricted region opposite a slot. By the orientation of the mesh so that its filaments are parallel to and perpendicular to the main dimensions of the patch, the mesh strands perpendicular to the protrusions will carry zero, or very low currents. Hence, the cutting of these finger-like protrusions will not substantially increase the total resistance of the patch.

The titanium mesh 12 may be conventionally fabricated of relatively fine, flexible strands with a density of about 20-50 strands per inch. The mesh thus forms a relatively fine foraminous screen that provides a high density of electrical contact points while retaining good flexibility to permit conformal shaping to the heart and minimize interference with heart activity after attachment.

Figure 2:
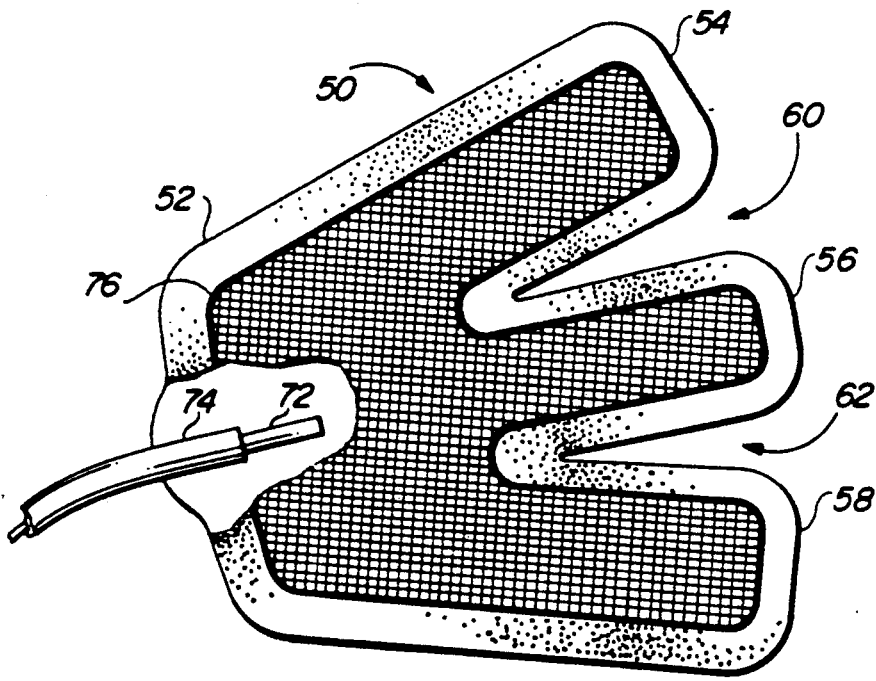
FIG. 2 is a plan view, partly broken away, taken from the contact side, of an alternative arrangement of a titanium mesh patch electrode in accordance with the invention.

FIG. 2 illustrates an alternative arrangement of a flexible planar patch electrode 50. Electrode 50 has a construction similar to that of electrode 10. However, the shape is somewhat modified to provide three protrusions in place of the two protrusions 22, 24 of electrode 10.

Electrode 50 has a generally rectangular base region 52 with three generally rectangular protrusions 54, 56, 58 extending longitudinally therefrom. The protrusions 54, 56, 58 are separated by two longitudinally extending intermediate slots 60, 62.

The additional protrusion and intermediate slot provide additional flexibility in locating and securing the electrode 50 relative to the surface of a heart. A lead 72 insulated by tube 74 is conductively secured to the titanium mesh centrally within the base region 52. The slots 60, 62 impose area restrictions on the passage of current from lead 72 to the protrusions 54 and 58. However, only the current for a single one of three protrusions must pass through the narrowed or restricted regions, both current densities and resistive losses in these regions are thus minimized.

As shown in FIG. 1, the mesh strands that are essentially orthogonal to conductive lead 32 may be contoured in an arcuate fashion, resulting in the mesh having strands substantially parallel to the length of the respective protrusions and strands substantially orthogonal to the width of the respective protrusions. This will be described in further detail with reference to FIG. 3. The mesh as shown in FIG. 2, on the other hand, is uniform throughout, and the shape of the patch may be obtained, for example, by following the contour of a template placed over the mesh so as to establish the final patch shape.

As previously noted, the present invention contemplates, but is not limited to, that the mesh 12 has orthogonally-oriented adjacent strands so that each mesh element is at least rectangular in form and preferably square, with each opposite side of the mesh element being, of course, of equal dimension.

Figure 3:
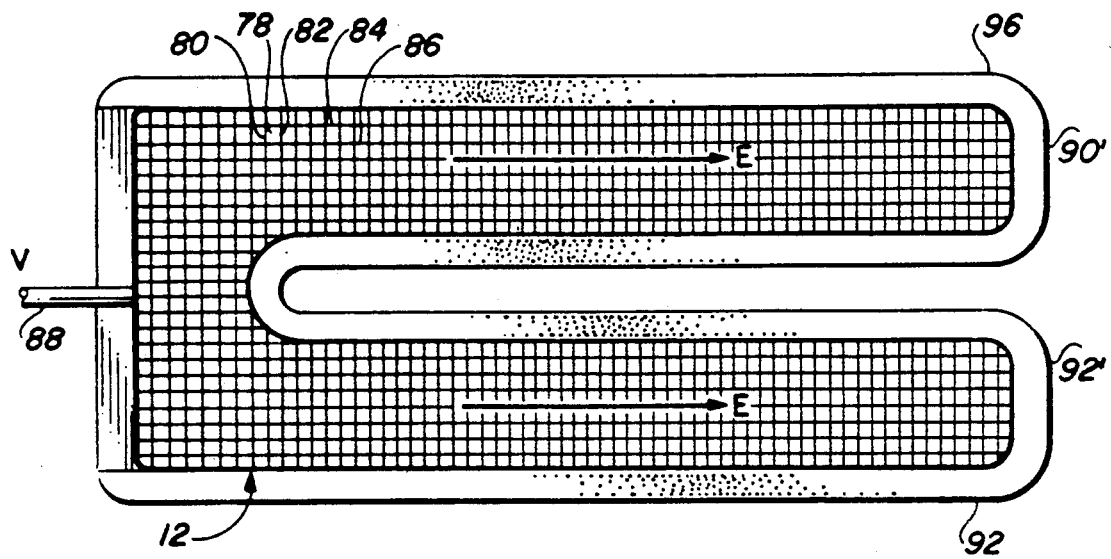
FIG. 3 is a plan view of a mesh patch electrode for cardiac defibrillation in accordance with the invention.

More specifically and as shown in detail in FIG. 3, mesh element 78 is bounded by vertical mesh lines 80 and 82 and horizontal mesh lines 84 and 86. As further noted in FIG. 3, the strands or mesh lines 80, 82, etc., extend longitudinally between the patch end which includes electrode 88 to the tips 90' and 92' of the fingers 90 and 92 respectively.

From FIG. 3, it is observed that strands 80, 82, etc., are oriented essentially parallel to the length of the patch, whereas strands 84, 86, etc., are orthogonal to strands 80 and 82, and to the length of the patch 10.

With an electric potential V applied to conductive lead 88 which is electrically coupled to the mesh strands an electric field perpendicular to such mesh strands, develops in the patch. The electric field identified as E in FIG. 3 illustrates the orthogonal nature of the field. With a uniform electric field distribution, resistive losses due to varying densities and fringing effects are minimized. The foregoing will be appreciated by inspection of FIG. 3 and FIG. 4. As noted from FIG. 3, the electric field E is substantially uniform throughout the mesh 12 and is maintained uniform in each of the fingers 90 and 92.

Figure 4:
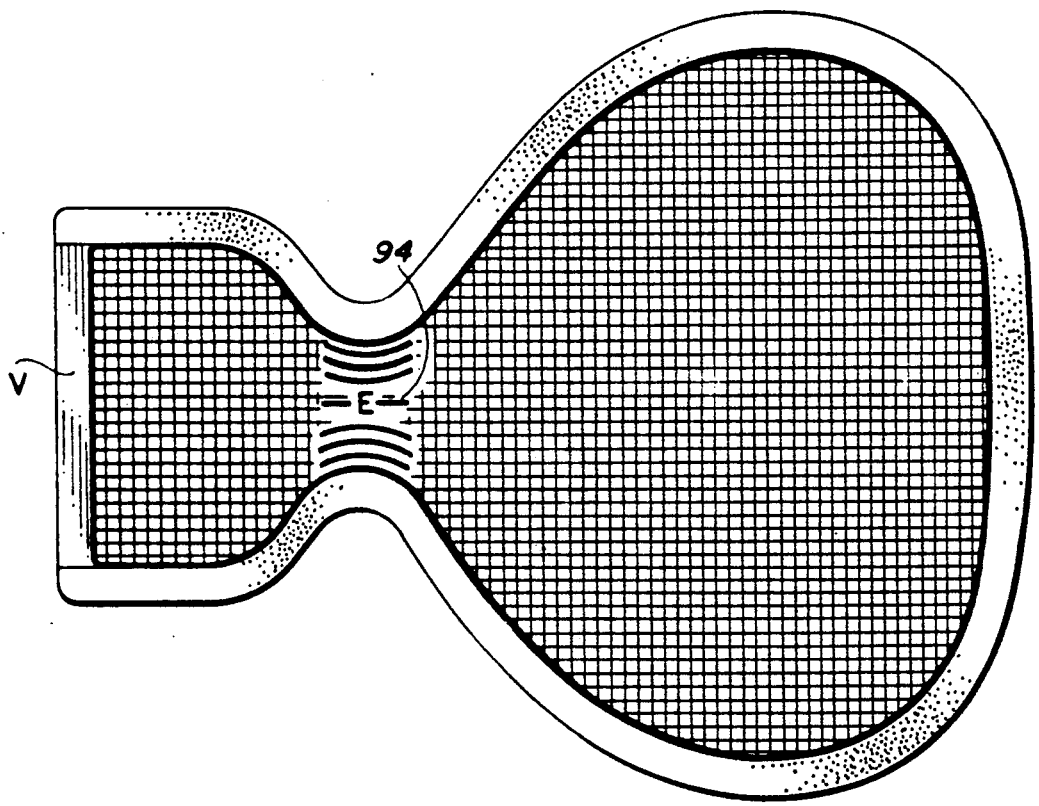
FIG. 4 is a plan view of a patch electrode for cardiac defibrillation illustrating the creation of unacceptable field concentrations which are avoided by the invention.

Accordingly, the design of the mesh of the present invention avoids the creation of the field concentrations at 94, which characterize the unacceptable designs, such as shown in FIG. 4. As noted, the present invention avoids the resistive losses arising out of the creation of non-uniform electric field patterns.

While there have been shown and described various alternative arrangements of a flexible, planar patch electrode for cardiac defibrillation in accordance with the invention for the purpose of enabling a person of ordinary skill in the art to make and use the invention, it should be appreciated that the invention is not limited thereto. Accordingly, any modifications, variations or equivalent arrangement within the scope of the attached claims should be considered to be within the scope of the invention.

What is claimed is:

1. A flexible, planar patch electrode for cardiac defibrillation comprising:
   a planar wire mesh having a contact side and an opposite insulation side, the wire mesh having a base region with a plurality of protrusions extending therefrom in a generally longitudinal direction, and with each adjacent pair of protrusions being separated by a generally longitudinally extending slot extending outward from the base region;
   an electrically insulated lead having a conductor conductively secured to the base region of the patch and centrally located thereon relative to a lateral direction perpendicular to the longitudinal direction;
   a flexible layer of insulation secured to the insulation side of the wire mesh and covering any noninsulated portion of the wire mesh; and
   an electrically insulated radiopaque marker disposed about the periphery of the wire mesh.

2. A patch electrode according to claim 1, wherein the wire mesh comprises titanium wire.

3. A patch electrode according to claim 1, wherein the contact side of the wire mesh has a surface area in the range of 2 to 4 square inches.

4. A patch electrode according to claim 1, wherein the contact side of the wire mesh has a surface area of substantially 3 square inches.

5. A patch electrode according to claim 1, wherein the wire mesh has a periphery and the layer of insulation has a periphery that extends beyond the periphery of the wire mesh to assure complete electrical isolation of the noncontact side of the wire mesh.

6. A patch electrode according to claim 1, wherein the lead is secured to the wire mesh in an orientation extending generally parallel to but on the opposite direction of the protrusions.

7. A patch electrode according to claim 1, wherein each protrusion has a rectangular shape.

8. A patch electrode according to claim 1, wherein there are exactly two protrusions extending from the base region.

9. A patch electrode according to claim 1, wherein there are exactly three protrusions extending from the base region.

10. The patch electrode according to claim 1, wherein the planar wire mesh further comprises a network of spaced-apart electrically conductive wire strands extending from the base region longitudinally along the protrusions, the spaced-apart electric wire strands oriented to provide a uniform electric field longitudinally along the mesh.

11. A flexible, planar patch electrode for cardiac defibrillation comprising:
   a planar foraminous screen having a periphery shaped to define a base region and a plurality of protrusions extending in a longitudinal direction from the base region with each pair of adjacent protrusions being separated by a longitudinally extending slot, the screen having a contact side for making physical electrically conductive contact with a heart and an opposite noncontact side;
   an insulated lead having a conductor with a noninsulated end secured to the base region of the screen midway between the sides thereof to provide good electrical communication with the screen at a location that minimizes electrical resistance in a path through the screen from the conductor to the laterally outermost protrusions, the conductor extending from the secured end in a direction opposite the protrusions;
   a layer of insulation secured to the noncontact side of the screen and covering the noninsulated end of the lead conductor, the layer of insulation having a periphery similar in shape to the periphery of the screen but extending beyond he periphery of the screen to assure electrical isolation on the noncontact side of the screen; and
   an electrically insulated radiopaque marker threaded about the periphery of the planar foraminous screen.

12. A flexible, planar patch electrode according to claim 11, wherein the contact side of the screen has a surface area in the range of 2–4 square inches.

13. A flexible, planar patch electrode according to claim 12, wherein the foraminous screen comprises titanium wire.

14. A flexible, planar patch electrode according to claim 12, wherein the foraminous screen comprises carbon.

15. A flexible, planar patch electrode according to claim 12, wherein the surface of the patch is covered with a non-toxic biocompatible material selected from the group consisting of metal carbide, metal nitride and metal oxide.

16. A flexible, planar patch electrode according to claim 12, wherein the layer of insulation comprises a Dacron reinforced Silastic sheet.

17. The flexible, planar patch electrode according to claim 11, wherein the planar patch electrode further comprises a network of spaced-apart electrically conductive wire strands extending from the base region longitudinally along the protrusions, the spaced-apart electric wire strands oriented to provide a uniform electric field longitudinally along the patch.

18. A single flexible, planar cardiac defibrillation electrode providing substantial area contact with a heart surface without significantly interfering with heart operation and without interfering with features on the surface of the heart comprising:

a wire mesh planar screen having a contact size and a noncontact side, an insulated lead a electrically connected at one end to the noncontact side of the planar screen and a layer of insulation covering the noncontact side of the planar screen and any noninsulated portion of the one end of the lead, the electrode having a base region connected to the lead and a plurality of protrusions each separated from an adjacent protrusion by an intermediate slot extending in a longitudinal direction from the base region to enable the base region and protrusions to be shaped into conformal contact with a surface of a heart while allowing any surface feature to be located within an intermediate slot to obtain a substantial surface contact area in the range of 2 to 4 square inches while avoiding significant interference with any motion of the contacted heart surface or features on the contacted heart surface; the wire mesh planar screen having a plurality of spaced-apart orthogonally oriented mesh strands wherein one of the strands are oriented in a direction parallel to the longitudinal direction of the protrusions so that other ones of the strands are oriented in a direction orthogonal to the longitudinal direction for generating a substantially uniform electric field in the protrusions essentially parallel to the longitudinal direction.

19. A single flexible, planar patch electrode for cardiac defibrillation comprising:

a planar wire mesh having a contact side and an opposite insulation side, the wire mesh having a base region with a plurality of protrusions extending therefrom in a generally longitudinal direction, and with each adjacent pair of protrusions being separated by a generally longitudinally extending slot extending outward from the base region, the planar wire mesh having a plurality of spaced-apart orthogonally oriented mesh strands wherein ones of the strands are oriented in a direction parallel to the longitudinal direction of the protrusions so that other ones of the strands are oriented in a direction orthogonal to the longitudinal direction for generating a substantially uniform electric field in the protrusions essentially parallel to the longitudinal direction;

an electrically insulated lead having a conductor conductively secured to the base region of the patch and centrally located thereon relative to a lateral direction perpendicular to the longitudinal direction; and a flexible layer of insulation secured to the insulation side of the wire mesh and covering any in an insulated portion of the wire mesh.

* * * * *